United States Patent [19]

Kraus et al.

[11] Patent Number: 5,635,375
[45] Date of Patent: Jun. 3, 1997

[54] METHOD OF INCREASING THE YIELD AND HEME SATURATION OF CYSTATHIONE β-SYNTHASE

[75] Inventors: Jan P. Kraus, Littleton; Vladimir Kery, Denver, both of Colo.

[73] Assignee: Regents of the University of Colorado, Boulder, Colo.

[21] Appl. No.: 370,036

[22] Filed: Jan. 9, 1995

[51] Int. Cl.$^6$ .............................. C12P 21/04; C12P 1/02
[52] U.S. Cl. ................................ 435/71.1; 435/183
[58] Field of Search .................................. 530/350, 385; 435/69.1, 69.4, 71.1, 183; 536/23.1

[56] References Cited

PUBLICATIONS

Kery et al. 1995 Archives Biochem Biophys 316(1):24–29.
Bowman et al 1980 Textbook of Pharmacology 2nd Edition. Blackwell Scientific Publications, Oxford. pp. 26.38–26.41.
Kraus et al 1994 Am J Human Genetics 55 (3 Suppl): A 174.
Kery et al 1994 J Biol Chem 269(41): 25283–25388.
Hart et al 1994 Applied Environ Microbiol 60(7): 2431–2437.
Ishikawa et al 1991 Eur J Biochem 202:161–165.
Hoffman et al 1990 Proc. Natl. Acad. Sci. 87: 8521–8525.
Smith et al 1990 J. Biol Chem 265(22): 13335–13343.
Haas et al 1991 J. Bacteriol 173(16): 5159–5167.
Springer et al 1987 Proc. Natl. Acad Sci 84:8961–8965.

*Primary Examiner*—Vasu S. Jagannathan
*Assistant Examiner*—Karen Carlson
*Attorney, Agent, or Firm*—Frederick W. Pepper

[57] ABSTRACT

A method of increasing the yield and heme saturation of hemoproteins in microorganisms. In this method, an effective amount of a heme precursor is added to a culture of hemoprotein producing microorganisms.

3 Claims, 6 Drawing Sheets

METHOD OF INCREASING THE YIELD AND HEME SATURATION OF CYSTATHIONE β-SYNTHASE

The U.S. Government has a paid-up license in this invention and the right in limited circumstances to require the patent owner to license others on reasonable terms as provided for by the terms of Grant No. HD08315 awarded by the National Institutes of Health.

FIELD OF THE INVENTION

The present invention relates to a method for the large scale production of hemoproteins, e.g. cystathionine β-synthase, hemoglobin, myoglobin, horseradish peroxidase, catalase, and heme oxygenase.

BACKGROUND OF THE INVENTION

Few foreign hemoproteins have been expressed in bacteria. Expression of active sperm whale [Springer and Sligar, *Proc. Natl. Acad. Sci. USA* 84: 8961-8965(1987)] and human [Varadarajan et al., *Proc. Natl. Acad. Sci.* 82: 5681-5684 (1985)] myoglobins, rat heme oxygenase [Ishikawa et al., *Eur. J. Biochem.* 303: 161-163 (1991)] and horseradish peroxidase C [Smith et al., *J. Biol Chem.* 265:13335-13343 (1990)] in *E. coli* have been reported. The myoglobins were purified to homogeneity from the crude bacterial extracts. Heme was either taken from the host bacteria [Varadarajan et al., *Proc. Natl. Acad. Sci.* 82: 5681-5684 (1985)] or incorporated into the apoprotein in vitro after the purification [Springer and Sligar, *Proc. Natl. Acad. Sci. USA* 84: 8961-8965(1987)]. Heme oxygenase, on the other hand, remained bound to the bacterial membranes and its heme saturation was uncertain [Ishikawa et al., *Eur. J. Biochem.* 303:161-163 (1991)]. Horseradish peroxidase C is produced in inclusion bodies in an insoluble inactive form containing only traces of heme and requires a tedious solubilization and in vitro reactivation [Smith et al., *J. Biol Chem.* 265:13335-13343 (1990)]. These examples demonstrate that expression of a hemoprotein in bacteria in an active, soluble form sufficiently saturated with heme often represents a difficult task.

It has been demonstrated recently that cystathionine β-synthase [L-serine hydrolyase (adding homocysteine); E. C. 4.2.1.22; CBS] is a hemoprotein [Bukovska et al., *Protein Express. Purif.* 5: 442-448 (1994); Kery et al., *J. Biol. Chem.* 269: 25283-25288 (1994)]. CBS is central to sulfur amino acid and S-adenosyl-L-methionine (AdoMet) metabolism in eukaryotes [Mudd et al., *The Metabolic Basis of Inherited Disease* 6th ed., pp 693-734, McGraw-Hill, New York (1989)]. It catalyzes the condensation of serine and homocysteine to cystathionine, the first step of the pyridoxal 5'-phosphate dependent (PLP) transsulfuration to cysteine. cDNAs encoding rat [Swaroop et al., *J. Biol. Chem.* 267: 11455-11461 (1992)] and human [Kraus et al., *Human Mol. Genet.* 2: 1633-1638 (1993)] CBS have been cloned and their amino acid sequences have been deduced. The human CBS cDNA was cloned into the pAX5⁻ plasmid and expressed in *Escherichia coli* XL1 Blue MR as a fusion protein with β-galactosidase. The fusion protein was cleaved by a specific protease and the released CBS was purified to homogeneity [Bukovska et al., *Protein Express. Purif.* 5: 442-448 (1994)].

Basic characteristics of the cloned human CBS were nearly identical to those determined previously for the rat and human liver enzyme [Bukovska et al., *Protein Express. Purif.* 5: 442-448 (1994)]: The enzyme required heme in addition to PLP for its function and was activated by AdoMet. Heme had to be present at the time of protein folding to be properly incorporated into the enzyme [Kery et al., *J. Biol. Chem.* 269: 25283-25288 (1994)].

Routine purification of the cloned human CBS yields enzyme which is an average only 20% saturated with heme. This low heme saturation substantially decreases the production of an active enzyme in *E. coli* because no in vitro method has been found which would allow reconstitution of the unsaturated enzyme with heme [Kery et al., *J. Biol. Chem.* 269: 25283-25288 (1994)].

SUMMARY OF THE INVENTION

The invention relates to increasing the yield and heme saturation of foreign hemoproteins such as, cystathionine β-synthase, hemoglobin, myoglobin, horseradish peroxidase, catalase, and heme oxygenase, in microorganisms. This invention is based upon the discovery that the use of a heme precursor, such as δ-aminolevulinate (δALA) or iron in $Fe^{3+}$ form, in culture medium increases heme synthesis during growth of the microorganisms. The culture media is any media containing 0.5-1.5% w/v peptone and 0.1-1% w/v of autolyzed yeast extract (e.g. Luria Broth) or 0.5-5% w/v tryptone, 0.1-1% w/v of autolyzed yeast extract (e.g. S.O.C. medium). The results are increased yield, activity, stability, and heme saturation of the hemoprotein facilitating large scale preparation of the foreign hemoprotein in a microorganism. For example, the microorganism, a bacteria, is supplemented with 0.3 mM δALA. The range of concentrations for heme precursor, δALA, can be from about 0.05 mM to about 5 mM. While growth of the bacteria does not change, a 50-fold elevation of the heme content per mg of total protein is observed in the cell extracts of δALA supplemented cells. The increase in heme biosynthesis depends on the overexpression of a heme acceptor—CBS. The δALA treatment results in 8 times more total CBS activity with a 3.5-fold higher yield of the purified recombinant enzyme, more than 68% saturated with heme.

"Expression vector" includes vectors which are capable of expressing DNA sequences contained therein where such sequences are operably linked to other sequences capable of effecting their expression. It is implied, although not explicitly stated, that expression vectors must be replicable in the host organisms either as episomes or as an integral part of a chromosomal DNA. Clearly, a lack of replication would render them effectively inoperable. In sum, "expression vector" is also given a functional definition. Generally, expression vectors of utility in DNA recombinant techniques are often in the form of "plasmids". Plasmids refer to either circular double stranded DNA molecules or circular single stranded DNA molecules, containing an origin of replication derived from a filamentous bacteriophage. These DNA molecules, in their vector form, are not linked to the chromosomes. Other effective vectors commonly used are phage and non-circular DNA. In the present specification, "plasmid" and "vector" are often used interchangeably. However, the invention is intended to include such other forms of expression vectors which serve equivalent functions and which are, or subsequently become, known.

Recombinant vectors and methodology disclosed herein are suitable for use in prokaryotic and eukaryotic expression systems. These expression systems include microbial strains, such as *E. coli* and *Saccharomyces cerevisiae*.

DETAILED DESCRIPTION OF THE INVENTION

When the human β-galactosidase-CBS fusion protein was expressed in *E. coli*, an enzyme was purified which was on average about 20% saturated with heme and the yield of active CBS was very low [Bukovska et al., *Protein Express. Purif.* 5: 441–448 (1994); Kery et al., *J. Biol. Chem.* 269:25283–25288 (1994)]. The present invention incorporates the heme moiety into the enzyme during the time of protein folding. In contrast, currently used methods cannot reconstitute the heme-unsaturated CBS with additional heme in vitro [Kery et al., *J. Biol. Chem.* 269: 25283–25288 (1994)]. Therefore, increased heme availability during protein synthesis and folding, as practiced by the invention, is the only way to increase the yield of active enzyme.

Porphyrin and heme biosynthesis in microorganisms and liver cells are affected by physiological factors such as oxygen tension [Jacobs et al., *Biochem. Biophys. Acta* 148: 645–654 (1967)], iron concentration [Doss and Philipp-Dormston, *Hoppe-Seyler's Z. Physiol. Chem.* 352:43–51 (1971)], and presence of lactate as a direct precursor of δALA [Doss and Philipp-Dormston, *FEBS Lett.* 40:173–175 (1974)]. The principal regulatory mechanism appears to be δALA synthase, the formation and activity of which is dictated by the end product, heme [Burnham and Lascelles, *Biochem. J.* 87:462–472 (1963)]. In the present invention, bypassing this regulatory step by addition of exogenous δALA results in a 10- to 30-fold increase of total porphyrin and a 3-fold increase in bacterial heme concentrations [Doss and Philipp-Dormston, *Hoppe-Seyler's Z. Physiol. Chem.* 352:725–733 (1971)].

As shown in Example 1, when added to the expression system, 0.3 mM δALA had no effect on cell growth. However, it increased the heme content per mg of total soluble protein in cell extracts up to 50-fold in 21 hours.

Figure 1:
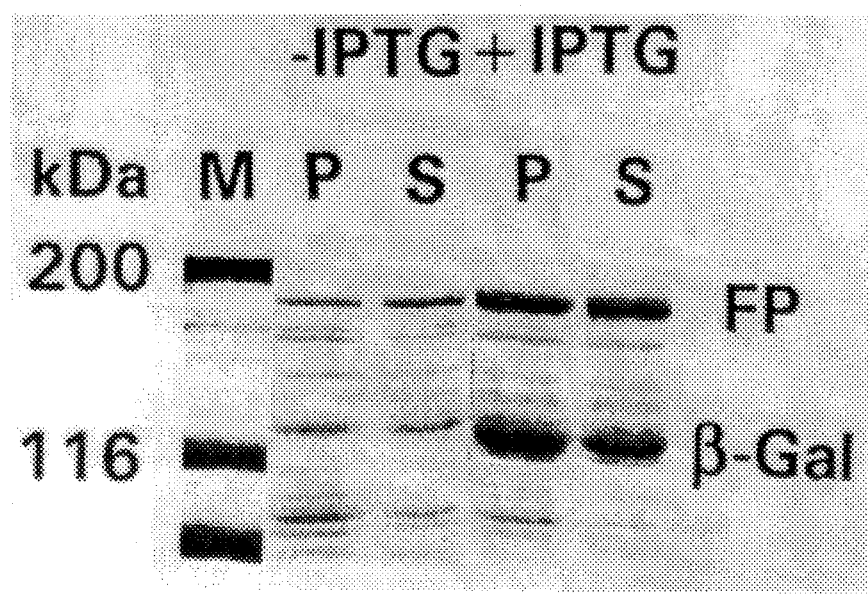
FIG. 1 represents a Commassie Brilliant Blue stained polyacrylamide gel showing the CBS-β-galactosidase fusion protein expressed in *E. coli*. M—Molecular weight protein standards; S-supernatant; P-pellet; FP-fusion protein; β-Gal-β-galactosidase.

The β-galactosidase-CBS fusion protein synthesis was specifically induced by IPTG (FIG. 1). Extracts from 21 h cell cultures were obtained as described in Example 1. The extracts were centrifuged and the pellets resuspended in the same volume of the lysis buffer as original cell extracts. Aliquots of the supernatants containing 20 μg of total protein in the same volumes of the pellet suspensions were run on a 9% SDS-polyacrylamide gel. In FIG. 1, the strong β-galactosidase band, absent in non-transformed XL1 strain, indicates that the fusion protein was partially cleaved into β-galactosidase and possibly other degradation products. Approximately half of the synthesized fusion protein was incorporated into the insoluble cell structures. This distribution was independent of the addition of δALA.

Figure 2:
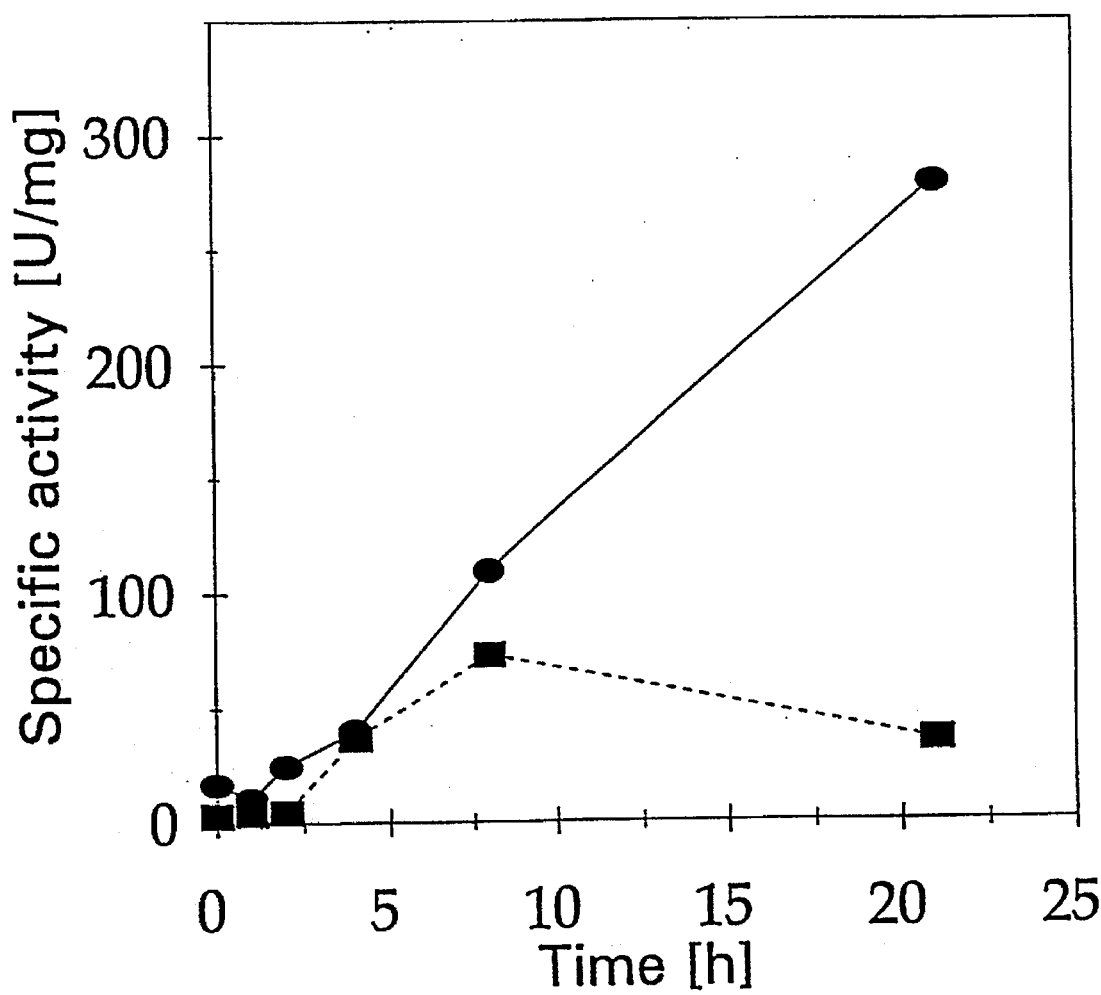
FIG. 2 is a graph showing that CBS specific activity of the fusion protein increases in δALA supplemented cells. (●—●) δALA$^+$ cultures; (■- - -■) δALA$^-$ cultures.

The time course of the increase of CBS specific activity of the fusion protein for the δALA$^+$ cultures is quite different from that of δALA$^-$ cultures (FIG. 2). The specific activity was calculated per mg of fusion protein determined by the Phosphorimager technique from Western blot of crude lysates, as described in Example 1. The specific activity increased continuously during the time of cultivation in δALA$^+$ cultures. On the other hand, δALA$^-$ cultures exhibited a maximum of the specific activity by 8 h of incubation and declined thereafter. These data show that CBS specific activity depends on the presence of heme precursor.

Figure 3:
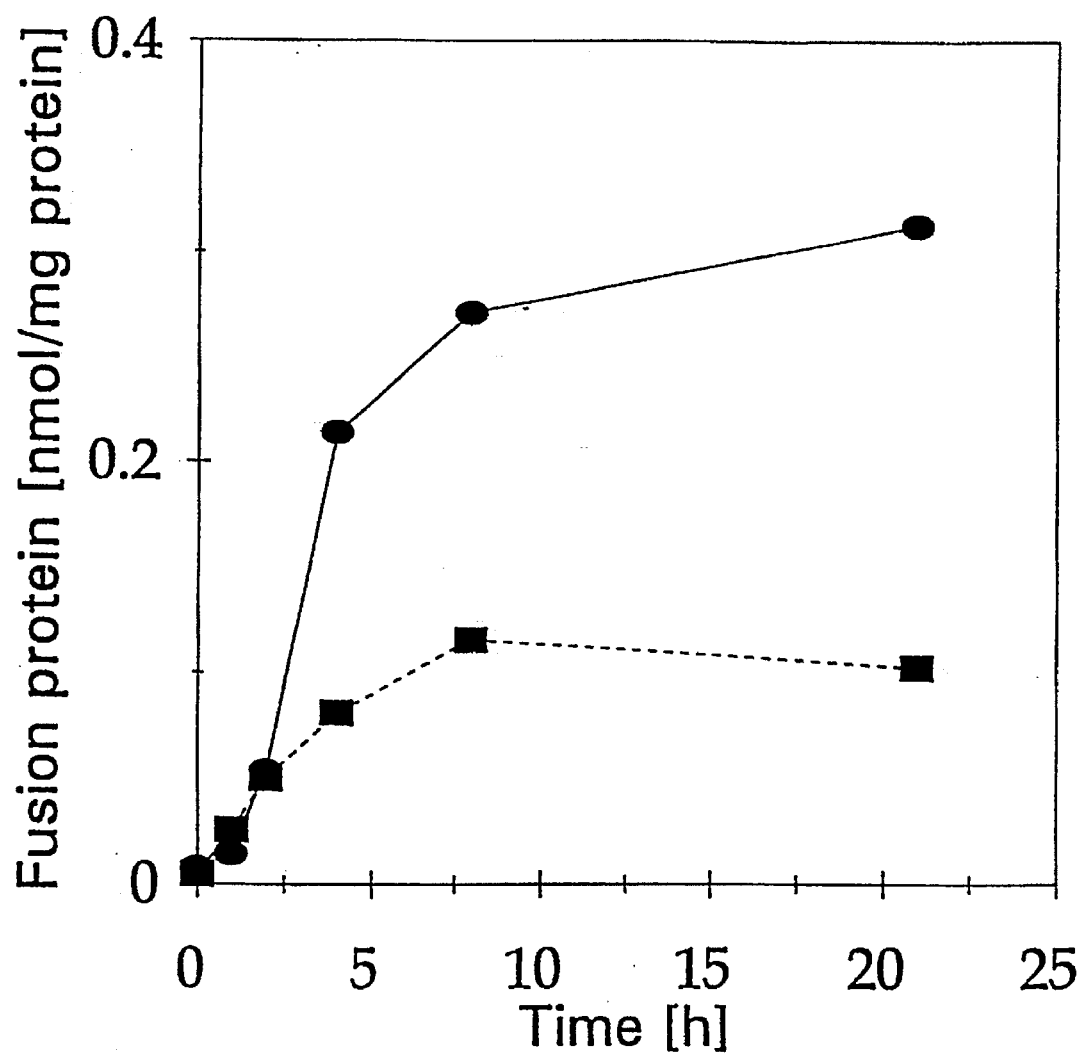
FIG. 3 is a graph showing the concentration of the human CBS-β-galactosidase fusion protein in crude *E. coli* extracts. (●—●) δALA$^+$ cultures; (■- - -■) δALA$^-$ cultures.

To find how the presence of δALA affects the biosynthesis and stability of the fusion protein in bacteria, the amounts of the fusion protein were determined that are in the soluble fraction of the bacterial lysate at different periods of cell growth (FIG. 3). Aliquots (150 ml) were taken from the 1 l original cell culture at 0, 1, 2, 4, 8, and 21 h after induction with IPTG. Amounts of the fusion protein were determined from the Western blot of crude cell extracts using the Phosphorimager and were calculated per mg of total soluble protein. Higher amounts of the fusion protein found in δALA$^+$ culture suggest either increased synthesis or decreased degradation of the fusion protein in comparison to that of controls.

Figure 4:
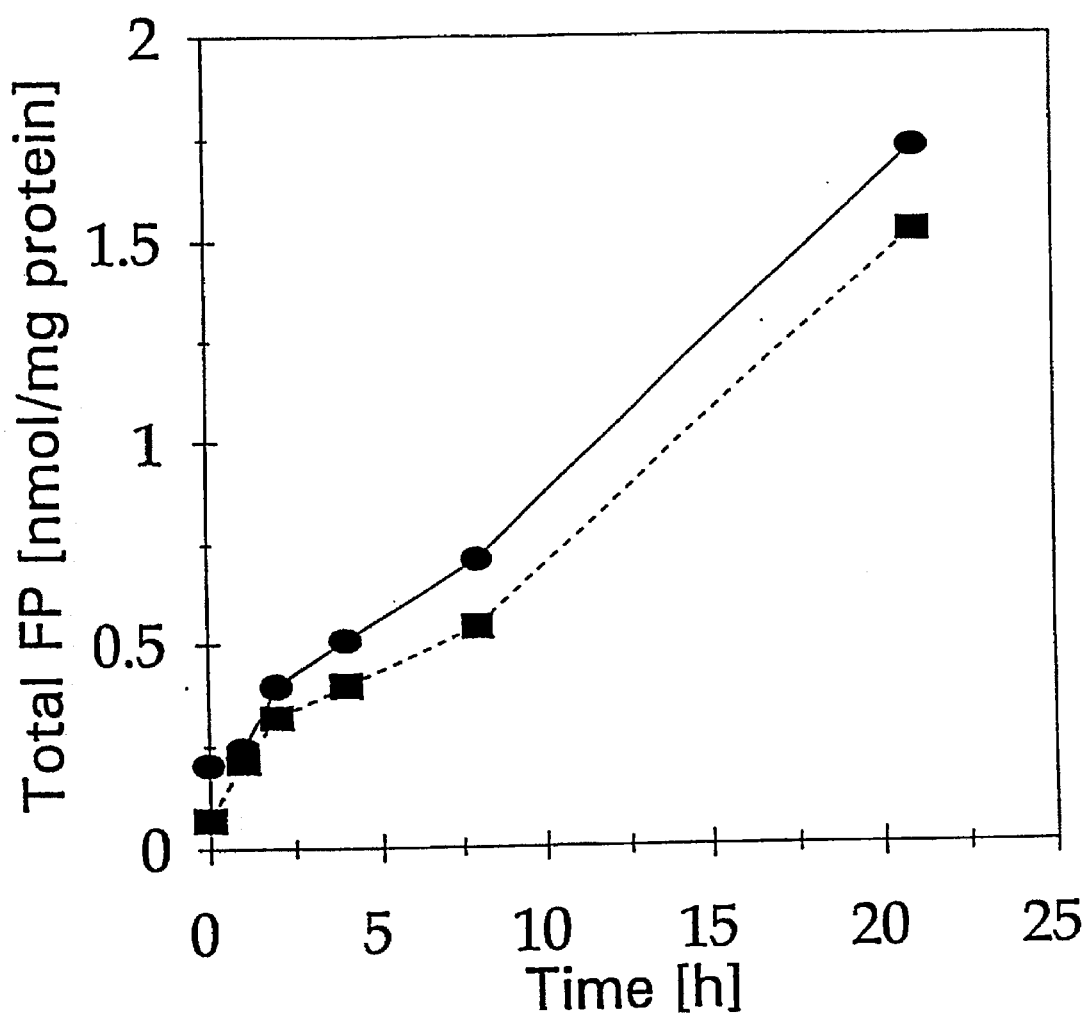
FIG. 4 is a graph showing the total fusion CBS-β-galactosidase protein synthesized in &rude extracts from *E. coli*. (●—●) δALA$^+$ cultures; (■- - -■) δALA$^-$ cultures.

To distinguish between the two possibilities, β-galactosidase activity was determined in the soluble cell extracts. This is the best estimate of the total fusion protein synthesized because it also includes its degradation products. These include mostly β-galactosidase and other products that may not be visible on Western blots, but may still be active. FIG. 4 shows that δALA supplementation does not affect the synthesis of the total fusion protein. Therefore, the increased content of the uncleaved fusion protein in the soluble cell extracts is due to increased stability of the hemoprotein towards protease cleavage rather than due to increased synthesis induced by δALA. The total fusion protein synthesized (FP) was estimated from β-galactosidase activity assayed in crude cell extracts and calculated per mg of total soluble protein. Purified β-galactosidase from *E. coli* (Sigma, #G-5635) was used to calibrate the assay.

Figure 5:
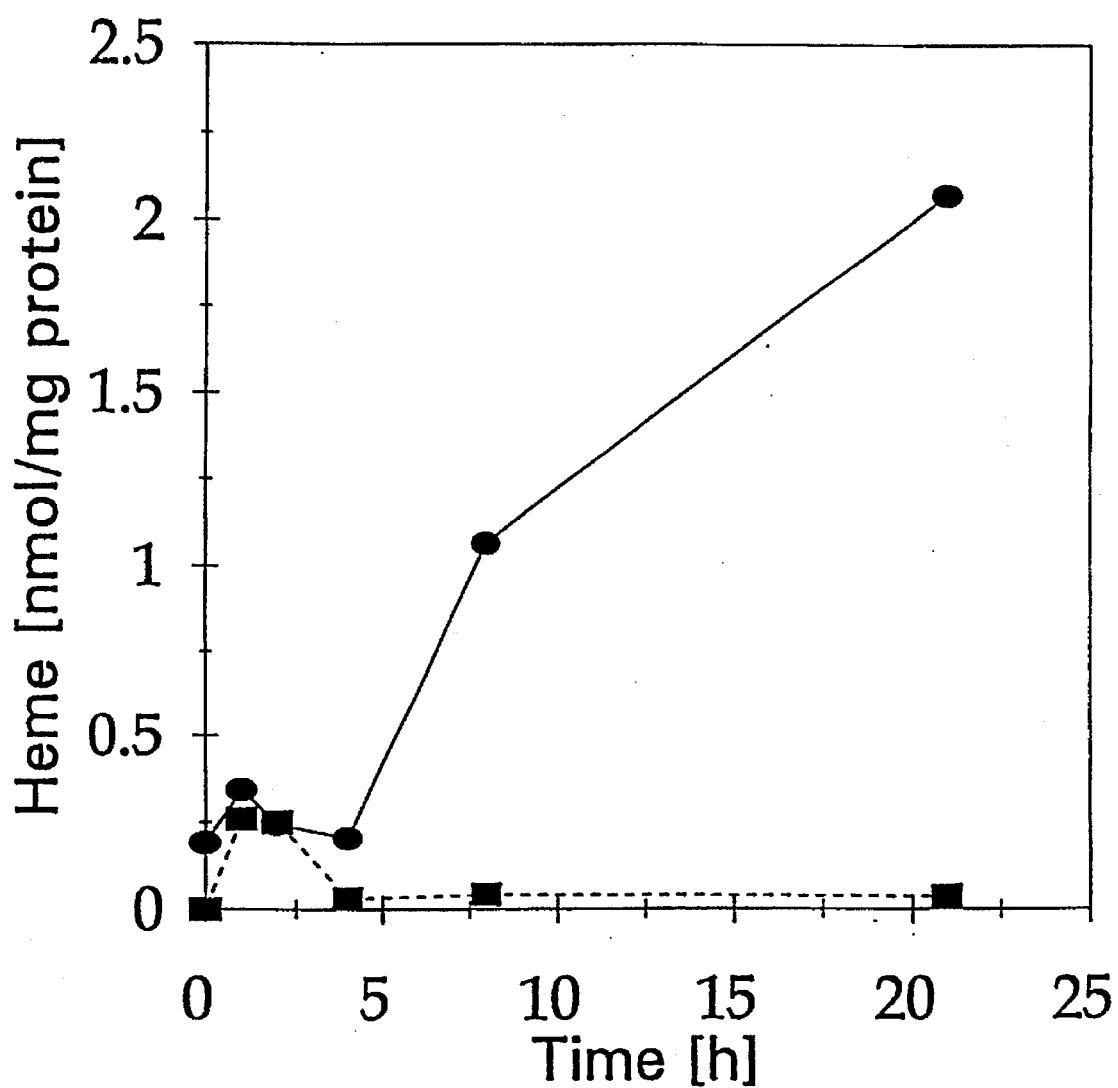
FIG. 5 is a graph showing the heme content in crude extracts from *E. coli* expressing the CBS-β-galactosidase fusion protein. (●—●) δALA$^+$ cultures; (■- - -■) δALA$^-$ cultures.

A striking difference was observed in heme production in δALA$^+$ and δALA$^-$ cultures (FIG. 5). The heme content was measured by the pyridine hemochromogen method [Kozich and Kraus, *Human Mutation* 1:113–123 (1992)] and calculated per mg of total soluble protein. The heme content in extracts from δALA-cultures remained low for the first 4 hrs and increased afterwards, following the total fusion protein synthesized (FIG. 4). On the other hand, from FIG. 5, it follows that the heme content in δALA$^-$ cultures increased only for the first 2 h after IPTG induction. Thereafter, it declined to about 30–40 pmol heme per mg of soluble protein—far less than the level of the total fusion protein synthesized (FIG. 4). These heme synthesis curves also resemble those of CBS activity shown in FIG. 2. The data show that the increased heme level was induced by the overproduction of the foreign hemoprotein when the heme precursor was available.

This conclusion is supported by the results presented in Table 1.

TABLE 1

Effect of δALA on heme synthesis and CBS specific activity in crude *E. coli* extracts.

| Plasmid | δALA[3] 0.3 mM | IPTG[4] 0.5 mM | Heme [pmol] per mg | Specific activity [Units] of total soluble | CBS synthesized [pmol] protein |
|---|---|---|---|---|---|
| β-Gal/CBS[1] | + | + | 2,100 | 4.5 | 1729 |
| β-Gal/CBS | + | − | 200 | 0.1 | 247 |
| β-Gal/CBS | − | + | 40 | 1.5 | 1520 |
| CBS[2] | + | + | 360 | 0.3 | 111 |
| CBS | − | + | 130 | 0.3 | 127 |

[1]*E. coli* XL1 Blue MR strain transformed with pAX5-7HCBS overproducing human CBS as a fusion protein with β-galactosidase [Bukovska et al., Protein Express. Purif. 5: 442–448 (1994)].
[2]*E. coli* DH5αFIQ strain transformed with pHCS3 producing low levels of non fused human CBS [Varadarajan et al., Proc. Natl. Acad. Sci. 82: 5681–5684 (1985)].
[3]δALA was added at the time of inoculation of the culture.
[4]IPTG was added when the bacterial suspension reached $A_{600} = 0.5$ (about 3.5 h from the time of inoculation). The measurements were performed in crude cell extracts 21 h after the IPTG induction.

The control δALA$^+$ culture in which CBS synthesis was not induced by IPTG did not overproduce heme. Further evidence was provided by the experiment in which another IPTG inducible plasmid construct, pHCS3 containing human CBS cDNA without any fusion partner was expressed in *E. coli* DH5αFIQ cells [Kozich and Kraus, *Human Mutation* 1:113–123 (1992)]. The cells were grown under the same conditions as the overproducing strain. They expressed about 10-fold less human CBS and tripled their heme production in δALA$^+$ culture. This increase is in agreement with the previously published observation of the effect of δALA on heme synthesis in *E. coli* [Doss and Philipp-Dormston, *Hoppe-Seyler's Z. Physiol. Chem.* 352:725–733 (1971); Philipp-Dormston and Doss, *Enzyme* 16:57–64 (1973)], but does not reach the heme production level in the CBS overproducing construct.

From these experiments it can be concluded that there is a regulatory feedback mechanism subsequent to the δALA synthase triggered by an increased intracellular concentration of free heme. In the absence of the heme acceptor, namely CBS, heme level remains at 200 pmol/mg of total soluble protein in δALA$^+$, IPTG$^-$ cultures. Similarly, δALA$^-$, IPTG$^+$ cultures which overproduce the heme acceptor but lack the heme precursor, retain the heme level at 30–40 pmol/ml of soluble total protein. It is possible that δALA dehydratase catalyzing the first biosynthetic step after δALA synthesis, is similarly regulated by hemin in bacteria as has been previously described for rabbit reticulocytes [Ibrahim et al., *Biochem. Biophys. Res. Commun.* 80: 722–728 (1978)].

The practical use of these results for a large scale purification of CBS hemoprotein is described in Table 2.

TABLE 2

Purification of human CBS expressed in *E. coli* in the absence or presence of δALA.

| Purification Step[1] | Total activity [U] | | Total protein [mg] | | Specific activity [U/mg] | |
|---|---|---|---|---|---|---|
| | δALA$^-$ | δALA$^+$ | δALA$^-$ | δALA$^+$ | δALA$^-$ | δALA$^+$ |
| 1. Crude extract | 5,481 | 13,938 | 3,654 | 3,030 | 1.5 | 4.5 |
| 2. Ammonium sulfate precipitation | 4,704 | 12,656 | 588 | 767 | 8 | 16.5 |
| 3. DE-52 cellulose[2] | 1,510 | 11,759 | 10 | 35 | 151 | 335 |

[1]δALA$^-$ cultures were prepared in 12 l of total suspension and harvested 4 h after IPTG induction (maximum of the specific activity). δALA$^+$ cultures were prepared in 6 l of total suspension containing 0.3 mM δALA and grown for 21 h. The volumes were adjusted to obtain about equal mass of total protein at the time when cells reached the maximum of CBS specific activity. Further procedures were performed as described in Materials and Methods.
[2]Homogeneity of the purified CBS by SDS-PAGE was >90%. Heme saturation was 23% and 69% for the enzyme purified from the bacteria grown in the absence and presence of δALA, respectively.

It clearly demonstrates that δALA supplementation increased the protein yield by up to 3.5-fold in comparison to a typical purification in which the same cells were incubated in the absence of δALA. This is in agreement with the estimate from Phosphorimager quantification of the crude extracts. The total yield of CBS activity, however, was about 8-fold higher, likely due to the increase of the enzyme saturation with heme from 23 to 69% It has been shown previously that heme is essential for the enzyme activity [Kery et al., *J. Biol. Chem.* 269:25283–25288 (1994)]. A greater stability against degradation and denaturation of the protein more saturated with heme also contributes to this result.

Figure 6:
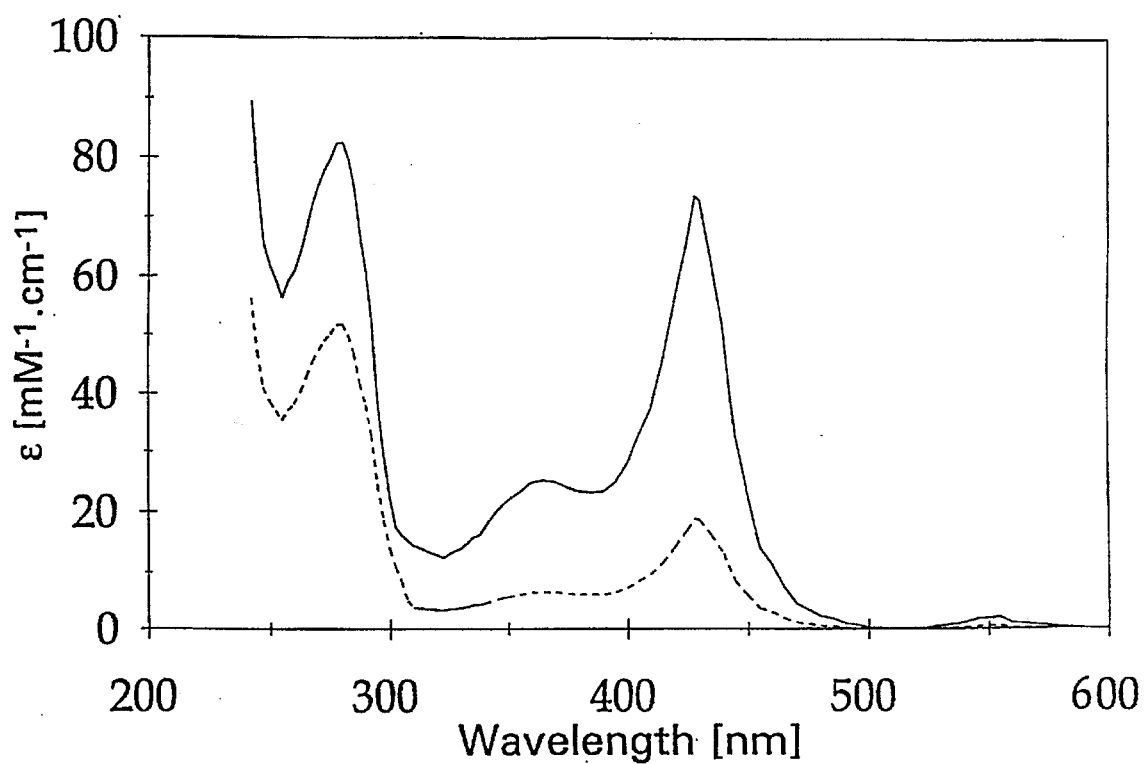
FIG. 6 shows the effect of δALA supplementation on the spectrum of cloned human CBS purified from *E. coli*. (—) CBS, 69% saturated with heme purified from δALA$^+$ culture; (- - -) CBS, 23% saturated with heme purified from δALA$^-$ cultures.

Increased heme saturation significantly effects the spectrum of the purified CBS (FIG. 6). The spectrum of 69% heme saturated enzyme is close to that of native CBS isolated from human liver [Kraus and Rosenberg, *Arch. Biolchem. Biophys.* 222: 44–52 (1983)]. The ratio $\epsilon_{428}/\epsilon_{280}$ reflecting the heme saturation was 0.76 for the liver enzyme compared to 0.89 and 0.35 for the cloned enzyme 69% and 23% saturated with heme, respectively.

These results suggest that a generally accepted mechanism of regulation of bacterial heme synthesis by the negative feedback of free heme on δALA synthesis may not be the only existing mechanism. Increased stability of CBS, improved yield and higher heme saturation will allow efficient large scale purification and further study of this cloned hemoprotein. These much improved results can be extrapolated to other hemoproteins expressed in *E. coli*.

The following example is presented to illustrate the present invention and to assist one of ordinary skill in making and using the same. The example is not intended in any way to otherwise limit the scope of the invention.

EXAMPLE

Human Liver CBS Expression And Purification

The coding region of human CBS cDNA [Kraus et al., *Human Mol. Genet.* 2: 1633–1638 (1993)] was inserted into the bacterial expression vector pAX5⁻ [Markmeyer et al., *Gene* 93: 129–134 (1990)] and expressed as a fusion protein with β-galactosidase [Bukovska et al., *Protein Express Purif.* 5: 442–448 (1994)]. The fusion protein consists of CBS linked to β-galactosidase by a collagen "hinge" region containing an endoproteinase Xa cleavage site. Its expression is controlled by the lac Z promoter inducible by 1-isopropylthio-β-D-galactopyranoside (IPTG). The plasmid construct was transformed into *E. coli* XL1 Blue MR (Stratagene, La Jolla, Calif.). Bacteria were grown at 37° C. aerobically in 1 l NZCYMT media (Gibco/BRL, Gaithersburg, Md.) containing 75 µg/ml ampicilin and 0.001% thiamine in the presence or absence of 0.3 mM δ-aminolevulinate (δALA) until they reached turbidity of 0.5 at 600 nm. IPTG was then added to 0.5 mM and the bacteria were grown further. Aliquots (150 ml) of the cell suspension were taken at 0, 1, 2, 4, 8, 21 h after adding IPTG. The cell suspensions were centrifuged at 4,000 xg for 15 min and washed with 50 mM Tris.HCl, pH 8.0, 10 mM EDTA, 1 mM 2-mercaptoethanol. The pellets were resuspended in 1 ml of lysis buffer (50 mM Tris.HCl buffer, pH 8.0 containing 10 mM EDTA and 10 mM mercaptoethanol) and frozen at −80° C. Cell extracts were prepared by lysozyme (0.5 mg/ml) treatment for 1 h at 4° C. followed by sonication at 50% duty for 30s using a model W-225 sonicator (Heat-ultrasonic).

The cells used for purification of CBS were grown under the same conditions. They were collected after 21 h. CBS was purified using previously described two step procedure [Bukovska et al., *Protein Express Purif.* 5: 442–448 (1994)]. Briefly, a cell extract was prepared from 30–40 g of wet cells and PLP (to 0.5 mM) was added. The β-galactosidase-CBS fusion protein was precipitated with ammonium sulfate (28% saturation) for 30 min at 4° C. The pellet was dissolved in 100 ml of Xa buffer (50 mM Tris.HCl, pH 8.0 containing 2 mM CaCl$_2$, 1 mM EDTA and 1 mM β-mercaptoethanol), dialyzed against the same buffer for 4 h and cleaved with endoproteinase Xa overnight. The solution containing cleaved CBS and then loaded onto a DE-52 cellulose (Whatman, Hillsboro, Oreg.) column (1.5×25 cm) and eluted with a linear gradient of 20 to 200 mM potassium phosphate, pH 7.0, containing 1 mM EDTA and 1 mM β-mercaptoethanol. The fractions containing >90% homogeneous enzyme, determined by SDS-PAGE, were collected, concentrated by ultrafiltration, frozen and stored in aliquots at −80° C.

Heme concentration was determined by the pyridine hemochromogen method after sodium dithionite reduction [Morrison and Horie, *Anal. Biochem.* 12: 77–82 (1965)], protein concentration was assayed by the Lowry method [Lowry et al., *J. Biol. Chem.* 193: 265–275 (1951)], and CBS activity was determined according to the previously described method [Kraus et al., *J. Biol. Chem.* 253: 6523–6528 (1978)]. Purified β-Galactosidase standard was obtained from Sigma (St. Louis, Mo.) and activity assayed as described by the manufacturer. Spectral measurements were performed on a Gilford-2400 spectrophotometer at 25° C.

Quantification of CBS fusion protein in crude extracts of transformed *E. coli* was performed on Western blots using a PhosphorImager (Molecular Dynamics, Sunnyvale, Calif.). Proteins were separated on a 9% SDS-PAGE and transferred to nitrocellulose membrane between semi-dry-carbon electrodes (Sartorius, Bohemia, N.Y.) at 0.8 mA/cm$^2$ for 1.5 h. The membrane was blocked for 1 h at room temperature with 5% lowfat milk in phosphate-buffered saline, pH 7.4 (PBS) and then incubated overnight at 4° C. with mouse anti-β-galactosidase antibodies (Sigma, St. Louis, Mo.) or rabbit antiCBS antisera (dilution 1:200) in Tris buffered saline (TBS), 10 mM TRIS-HCl, 150 mMNaCl, pH 7.4, containing 3% bovine serum albumin. After washing with TBS containing 0.05% Tween-20, the blot was incubated with $^{125}$I-Protein A (Amersham, Arlington Heights, Ill.), 30 mCi/mg, diluted 1:1000 in TBS, pH 7.4, containing 3% bovine serum albumin. The intensity of the bands corresponding to the fusion protein and β-galactosidase were quantitated using the Phosphorimager and the amounts of the protein were determined using purified β-galactosidase (Sigma, #G-5635) or purified CBS standards (range 20–400 ng/lane).

The invention described herein is useful as a simple, inexpensive approach for improving the large scale production of hemoproteins.

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the example contained in the foregoing description.

What is claimed is:

1. A method of increasing the yield and heme saturation of cystathionine β-synthase from a microorganism, which includes forming a cystathionine β-synthase producing microorganism in a suitable cell culture medium, maintaining the microorganism under conditions conducive to cystathionine β-synthase production, and isolating the cystathionine β-synthase from the microorganism, wherein the improvement comprises:

introducing a heme synthesis increasing heme precursor into the microorganism in an effective heme synthesis increasing amount.

2. The method of claim 1 wherein the microorganism is *E. Coli*.

3. The method of claim 1 wherein the heme precursor comprises δ-aminolevulinate.

\* \* \* \* \*